US009795324B2

(12) United States Patent
Sales et al.

(10) Patent No.: US 9,795,324 B2
(45) Date of Patent: Oct. 24, 2017

(54) SYSTEM FOR MONITORING INDIVIDUALS AS THEY AGE IN PLACE (71) Applicant: Vision Service Plan, Rancho Cordova, CA (US)

(72) Inventors: Jay William Sales, Citrus Heights, CA (US); Richard Chester Klosinski, Jr., Sacramento, CA (US); Matthew Allen Workman, Sacramento, CA (US); Meghan Kathleen Murphy, Davis, CA (US); Matthew David Steen, Sacramento, CA (US)

(73) Assignee: Vision Service Plan, Rancho Cordova, CA (US)

( * ) Notice: Subject to any disclaimer, the term of this patent is extended or adjusted under 35 U.S.C. 154(b) by 10 days.

(21) Appl. No.: 14/562,454

(22) Filed: Dec. 5, 2014

(65) Prior Publication Data

US 2016/0071390 A1    Mar. 10, 2016

Related U.S. Application Data (60) Provisional application No. 62/046,406, filed on Sep. 5, 2014.

(51) Int. Cl.
*A61B 5/11*    (2006.01)
*A61B 5/00*    (2006.01)
(Continued)

(52) U.S. Cl.
CPC .............. *A61B 5/112* (2013.01); *A61B 3/112* (2013.01); *A61B 5/0002* (2013.01);
(Continued)

(58) Field of Classification Search
CPC ....................................... A61L 35/11
(Continued)

(56) References Cited

U.S. PATENT DOCUMENTS 3,972,038 A    7/1976    Fletcher et al.
4,100,401 A    7/1978    Tutt et al.
(Continued)

FOREIGN PATENT DOCUMENTS

WO    2005015163    2/2005
WO    2005094667    10/2005
(Continued)

OTHER PUBLICATIONS

Invitation to Pay Additional Search Fees, dated Nov. 4, 2015, from corresponding International Application Serial No. PCT/US2015/048612.
(Continued)

*Primary Examiner* — Kavita Padmanabhan
*Assistant Examiner* — Tionna Burke
(74) *Attorney, Agent, or Firm* — Brient Globerman, LLC; Kyle M. Globerman (57) ABSTRACT A computer-implemented method, and related system, for monitoring the wellbeing of an individual by providing eyewear that includes at least one sensor for monitoring the motion of the user. In various embodiments, the system receives data generated by the at least one sensor, uses the data to determine the user's movements using the received data, and compares the user's movements to previously established movement patterns of the user. If the system detects one or more inconsistencies between the user's current movements as compared to the previously established movement patterns of the user, the system may notify the user or a third party of the detected one or more inconsistencies. The system may similarly monitor a user's compliance with a medical regime and notify the user or a third party of the user's compliance with the regime.

19 Claims, 4 Drawing Sheets (51) Int. Cl.

| | | |
|---|---|---|
| *A61B 3/11* | (2006.01) | |
| *A61B 5/0402* | (2006.01) | |
| *A61B 5/0476* | (2006.01) | |
| *A61B 5/103* | (2006.01) | |
| *A61B 5/1171* | (2016.01) | |
| *A61B 5/16* | (2006.01) | |
| *A61B 7/04* | (2006.01) | |
| *G09B 5/00* | (2006.01) | |
| *A61B 5/1455* | (2006.01) | |
| *G06K 9/00* | (2006.01) | |
| *G06K 9/62* | (2006.01) | |
| *G08B 21/04* | (2006.01) | |
| *A63B 24/00* | (2006.01) | |
| *G09B 5/06* | (2006.01) | |
| *G09B 19/00* | (2006.01) | |
| *G06F 19/00* | (2011.01) | |
| *A61F 2/76* | (2006.01) | |
| *A61B 5/0205* | (2006.01) | |
| *A61B 5/024* | (2006.01) | |
| *A61B 5/053* | (2006.01) | |
| *A61B 5/08* | (2006.01) | |
| *G02C 11/00* | (2006.01) | |

(52) U.S. Cl.
CPC .......... *A61B 5/0022* (2013.01); *A61B 5/0077* (2013.01); *A61B 5/0402* (2013.01); *A61B 5/0476* (2013.01); *A61B 5/1032* (2013.01); *A61B 5/1103* (2013.01); *A61B 5/1114* (2013.01); *A61B 5/1116* (2013.01); *A61B 5/1128* (2013.01); *A61B 5/1176* (2013.01); *A61B 5/14552* (2013.01); *A61B 5/165* (2013.01); *A61B 5/4076* (2013.01); *A61B 5/4266* (2013.01); *A61B 5/443* (2013.01); *A61B 5/486* (2013.01); *A61B 5/4884* (2013.01); *A61B 5/6803* (2013.01); *A61B 5/7246* (2013.01); *A61B 5/7278* (2013.01); *A61B 7/04* (2013.01); *A63B 24/0062* (2013.01); *G06F 19/3481* (2013.01); *G06K 9/00348* (2013.01); *G06K 9/00617* (2013.01); *G06K 9/00664* (2013.01); *G06K 9/6201* (2013.01); *G08B 21/0423* (2013.01); *G08B 21/0461* (2013.01); *G08B 21/0476* (2013.01); *G09B 5/00* (2013.01); *G09B 5/06* (2013.01); *G09B 19/0092* (2013.01); *A61B 5/024* (2013.01); *A61B 5/0205* (2013.01); *A61B 5/0531* (2013.01); *A61B 5/0816* (2013.01); *A61B 5/1118* (2013.01); *A61B 5/7282* (2013.01); *A61B 2560/0475* (2013.01); *A61B 2562/0219* (2013.01); *A61B 2562/0223* (2013.01); *A61B 2562/0257* (2013.01); *A61B 2576/00* (2013.01); *A61F 2/76* (2013.01); *A61F 2002/7695* (2013.01); *G02C 11/10* (2013.01)

(58) Field of Classification Search
USPC ........................................................ 715/236
See application file for complete search history.

(56) References Cited

U.S. PATENT DOCUMENTS

| | | |
|---|---|---|
| 4,195,642 A | 4/1980 | Price et al. |
| 4,281,663 A | 8/1981 | Pringle |
| 4,407,295 A | 10/1983 | Steuer et al. |
| 4,855,942 A | 8/1989 | Bianco |
| 4,878,749 A | 11/1989 | McGee |
| 4,919,530 A | 4/1990 | Hyman |
| 5,422,816 A | 6/1995 | Sprague et al. |
| 5,452,480 A | 9/1995 | Ryden |
| 5,585,871 A | 12/1996 | Linden |
| 5,670,872 A | 9/1997 | Van De Walle et al. |
| 5,746,501 A | 5/1998 | Chien et al. |
| 5,891,042 A | 4/1999 | Sham et al. |
| 5,931,764 A | 8/1999 | Freeman et al. |
| 5,966,680 A | 10/1999 | Butnaru |
| 5,976,083 A | 11/1999 | Richardson |
| 6,013,007 A | 1/2000 | Root et al. |
| 6,183,425 B1 | 2/2001 | Whalen et al. |
| 6,218,958 B1 | 4/2001 | Eichstaedt et al. |
| 6,241,684 B1 | 6/2001 | Amano et al. |
| 6,325,507 B1 | 12/2001 | Jannard et al. |
| 6,381,482 B1 | 4/2002 | Jayaraman et al. |
| 6,431,705 B1 | 8/2002 | Linden et al. |
| 6,439,067 B1 | 8/2002 | Goldman et al. |
| 6,513,532 B2 | 2/2003 | Mault et al. |
| 6,532,298 B1 | 3/2003 | Cambier et al. |
| 6,736,759 B1 | 5/2004 | Stubbs et al. |
| 6,769,767 B2 | 8/2004 | Swab et al. |
| 6,783,501 B2 | 8/2004 | Takahashi et al. |
| 6,790,178 B1 | 9/2004 | Mault et al. |
| 6,812,845 B2 | 11/2004 | Yuzuki et al. |
| 7,187,960 B2 | 3/2007 | Abreu |
| 7,192,136 B2 | 3/2007 | Howell et al. |
| 7,255,437 B2 | 8/2007 | Howell et al. |
| 7,376,238 B1 | 5/2008 | Rivas et al. |
| 7,380,936 B2 | 6/2008 | Howell et al. |
| 7,400,257 B2 | 7/2008 | Rivas |
| 7,401,918 B2 | 7/2008 | Howell et al. |
| 7,438,410 B1 | 10/2008 | Howell et al. |
| 7,454,002 B1 | 11/2008 | Gardner et al. |
| 7,457,434 B2 | 11/2008 | Azar |
| 7,481,531 B2 | 1/2009 | Howell et al. |
| 7,488,294 B2 | 2/2009 | Torch |
| 7,500,746 B1 | 3/2009 | Howell et al. |
| 7,500,747 B2 | 3/2009 | Howell et al. |
| 7,515,054 B2 | 4/2009 | Torch |
| 7,543,934 B2 | 6/2009 | Howell et al. |
| 7,581,833 B2 | 9/2009 | Howell et al. |
| 7,621,634 B2 | 11/2009 | Howell et al. |
| 7,634,379 B2 | 12/2009 | Noble |
| 7,648,463 B1 | 1/2010 | Elhag et al. |
| 7,677,723 B2 | 3/2010 | Howell et al. |
| 7,771,046 B2 | 8/2010 | Howell et al. |
| 7,792,552 B2 | 9/2010 | Thomas et al. |
| 7,793,361 B2 | 9/2010 | Ishihara et al. |
| 7,806,525 B2 | 10/2010 | Howell et al. |
| 7,857,772 B2 | 12/2010 | Bouvier et al. |
| 7,922,321 B2 | 4/2011 | Howell et al. |
| 7,987,070 B2 | 7/2011 | Kahn et al. |
| 8,109,629 B2 | 2/2012 | Howell et al. |
| 8,188,868 B2 | 5/2012 | Case |
| 8,294,581 B2 | 10/2012 | Kamen |
| 8,303,311 B2 | 11/2012 | Forest |
| 8,337,013 B2 | 12/2012 | Howell et al. |
| 8,384,617 B2 | 2/2013 | Braun et al. |
| 8,430,507 B2 | 4/2013 | Howell et al. |
| 8,449,471 B2 | 5/2013 | Tran |
| 8,465,151 B2 | 6/2013 | Howell et al. |
| 8,494,507 B1 | 7/2013 | Tedesco et al. |
| 8,500,271 B2 | 8/2013 | Howell et al. |
| 8,510,166 B2 | 8/2013 | Neven |
| 8,540,583 B2 | 9/2013 | Leech |
| 8,568,313 B2 | 10/2013 | Sadhu |
| 8,594,971 B2 | 11/2013 | Keal et al. |
| 8,620,600 B2 | 12/2013 | Vock et al. |
| 8,630,633 B1 | 1/2014 | Tedesco et al. |
| 8,634,701 B2 | 1/2014 | Kang et al. |
| 8,647,270 B2 | 2/2014 | Leboeuf et al. |
| 8,690,750 B2 | 4/2014 | Krueger |
| 8,696,113 B2 | 4/2014 | Lewis |
| 8,733,928 B1 | 5/2014 | Lewis |
| 8,750,971 B2 | 6/2014 | Tran |
| 8,764,651 B2 | 7/2014 | Tran |
| 8,849,610 B2 | 9/2014 | Molettiere et al. |
| 8,892,401 B2 | 11/2014 | Yuen et al. |
| 8,905,542 B2 | 12/2014 | Howell et al. |

(56) References Cited

U.S. PATENT DOCUMENTS

| | | | |
|---|---|---|---|
| 8,911,087 B2 | 12/2014 | Publicover et al. | |
| 8,920,332 B2 | 12/2014 | Hong et al. | |
| 8,931,896 B2 | 1/2015 | Blum et al. | |
| 8,941,560 B2 | 1/2015 | Wong et al. | |
| 8,961,415 B2 | 2/2015 | Leboeuf et al. | |
| 8,964,298 B2 | 2/2015 | Haddick et al. | |
| 9,001,427 B2 | 4/2015 | Jacobs et al. | |
| 9,005,129 B2 | 4/2015 | Venkatraman et al. | |
| 9,007,220 B2 | 4/2015 | Johns et al. | |
| 9,028,405 B2 | 5/2015 | Tran | |
| 9,033,493 B2 | 5/2015 | Howell et al. | |
| 9,035,970 B2 | 5/2015 | Lamb et al. | |
| 9,064,342 B2 | 6/2015 | Yuen et al. | |
| 9,113,794 B2 | 8/2015 | Hong et al. | |
| 9,113,795 B2 | 8/2015 | Hong et al. | |
| 9,144,405 B2 | 9/2015 | Kim et al. | |
| 9,215,290 B2 | 12/2015 | Yuen et al. | |
| 9,235,064 B2 | 1/2016 | Lewis | |
| 9,239,473 B2 | 1/2016 | Lewis | |
| 9,241,635 B2 | 1/2016 | Yuen et al. | |
| 9,244,293 B2 | 1/2016 | Lewis | |
| 9,520,638 B2 | 12/2016 | Baringer et al. | |
| 2001/0031031 A1 | 10/2001 | Ogawa et al. | |
| 2002/0151810 A1 | 10/2002 | Wong et al. | |
| 2003/0195398 A1 | 10/2003 | Suzuki et al. | |
| 2005/0033200 A1 | 2/2005 | Soehren et al. | |
| 2005/0036103 A1 | 2/2005 | Bloch | |
| 2005/0054942 A1* | 3/2005 | Melker | A61B 5/082 600/532 |
| 2006/0115130 A1 | 6/2006 | Kozlay | |
| 2007/0273611 A1 | 11/2007 | Torch | |
| 2008/0137916 A1 | 6/2008 | Lauper et al. | |
| 2009/0069720 A1* | 3/2009 | Beck | A61B 5/4866 600/587 |
| 2009/0127339 A1* | 5/2009 | Needhan | G06F 19/3456 235/454 |
| 2009/0195747 A1 | 8/2009 | Insua | |
| 2009/0227853 A1 | 9/2009 | Wijesiriwardana | |
| 2009/0267805 A1 | 10/2009 | Jin et al. | |
| 2010/0042430 A1 | 2/2010 | Bartfeld | |
| 2010/0045928 A1 | 2/2010 | Levy | |
| 2010/0110368 A1 | 5/2010 | Chaum | |
| 2010/0136508 A1 | 6/2010 | Zekhtser | |
| 2010/0280336 A1 | 11/2010 | Giftakis et al. | |
| 2010/0302041 A1* | 12/2010 | Malik | G08B 21/04 340/573.1 |
| 2010/0308999 A1 | 12/2010 | Chornenky | |
| 2010/0332571 A1 | 12/2010 | Healey et al. | |
| 2011/0169932 A1 | 7/2011 | Mula et al. | |
| 2011/0224505 A1 | 9/2011 | Sadhu | |
| 2012/0021806 A1 | 1/2012 | Maltz | |
| 2012/0029367 A1 | 2/2012 | Hobeika | |
| 2012/0127423 A1 | 5/2012 | Blum et al. | |
| 2012/0133885 A1 | 5/2012 | Howell et al. | |
| 2012/0135384 A1 | 5/2012 | Nakao | |
| 2012/0142443 A1 | 6/2012 | Savarese et al. | |
| 2012/0169990 A1 | 7/2012 | Burnstein | |
| 2012/0206485 A1* | 8/2012 | Osterhout | G02B 27/0093 345/633 |
| 2012/0310442 A1 | 12/2012 | Doutaz et al. | |
| 2013/0009907 A1 | 1/2013 | Rosenberg et al. | |
| 2013/0024022 A1 | 1/2013 | Bowers | |
| 2013/0041590 A1 | 2/2013 | Burich et al. | |
| 2013/0050258 A1 | 2/2013 | Liu et al. | |
| 2013/0096397 A1 | 4/2013 | Kiso et al. | |
| 2013/0138413 A1 | 5/2013 | Finch et al. | |
| 2013/0157232 A1 | 6/2013 | Ehrenkranz | |
| 2013/0242262 A1 | 9/2013 | Lewis | |
| 2013/0274587 A1 | 10/2013 | Coza et al. | |
| 2013/0274904 A1 | 10/2013 | Coza et al. | |
| 2013/0307670 A1 | 11/2013 | Ramaci | |
| 2013/0329183 A1 | 12/2013 | Blum et al. | |
| 2013/0345168 A1* | 12/2013 | Kim | A61K 8/736 514/55 |
| 2014/0028456 A1 | 1/2014 | Sadhu | |
| 2014/0031703 A1 | 1/2014 | Rayner et al. | |
| 2014/0063242 A1 | 3/2014 | Hanina et al. | |
| 2014/0073081 A1 | 3/2014 | Wang | |
| 2014/0078049 A1 | 3/2014 | Parshionikar | |
| 2014/0085190 A1* | 3/2014 | Erinjippurath | G02B 27/0172 345/156 |
| 2014/0135593 A1 | 5/2014 | Jayalth et al. | |
| 2014/0142459 A1 | 5/2014 | Jayalth et al. | |
| 2014/0159862 A1 | 6/2014 | Yang et al. | |
| 2014/0207264 A1 | 7/2014 | Quy | |
| 2014/0218281 A1 | 8/2014 | Amayeh et al. | |
| 2014/0228649 A1 | 8/2014 | Rayner et al. | |
| 2014/0229220 A1 | 8/2014 | Yuen et al. | |
| 2014/0247145 A1 | 9/2014 | Proud | |
| 2014/0340221 A1 | 11/2014 | Yuen et al. | |
| 2014/0346158 A1 | 11/2014 | Matthews | |
| 2014/0375452 A1 | 12/2014 | Yuen et al. | |
| 2014/0375470 A1 | 12/2014 | Malveaux | |
| 2014/0378872 A1 | 12/2014 | Hong et al. | |
| 2015/0057512 A1 | 2/2015 | Kapoor | |
| 2015/0085245 A1 | 3/2015 | Howell et al. | |
| 2015/0088464 A1 | 3/2015 | Yuen et al. | |
| 2015/0173631 A1 | 6/2015 | Richards et al. | |
| 2015/0179050 A1 | 6/2015 | Katingari et al. | |
| 2015/0185506 A1 | 7/2015 | Lewis | |
| 2015/0212329 A1 | 7/2015 | Sugihara et al. | |
| 2015/0223805 A1 | 8/2015 | Whitman et al. | |
| 2015/0281879 A1 | 10/2015 | Saadi | |
| 2015/0287338 A1 | 10/2015 | Wells et al. | |
| 2015/0332149 A1 | 11/2015 | Kolb et al. | |
| 2015/0342482 A1 | 12/2015 | Carrara | |
| 2016/0007849 A1 | 1/2016 | Krueger | |
| 2016/0034042 A1 | 2/2016 | Joo | |
| 2016/0041404 A1 | 2/2016 | Palermo et al. | |
| 2016/0041613 A1 | 2/2016 | Klanner et al. | |
| 2016/0117937 A1 | 4/2016 | Penders et al. | |

FOREIGN PATENT DOCUMENTS

| | | |
|---|---|---|
| WO | 2008073806 | 6/2008 |
| WO | 2010006370 | 1/2010 |
| WO | 2010062479 | 6/2010 |
| WO | 2010062481 | 6/2010 |
| WO | 2011086466 | 7/2011 |
| WO | 2012041485 | 4/2012 |
| WO | 2013188343 | 12/2013 |
| WO | 2014108481 | 7/2014 |
| WO | 2014144918 | 9/2014 |
| WO | 2014144940 | 9/2014 |
| WO | 2014170280 | 10/2014 |
| WO | 2014188244 | 11/2014 |
| WO | 2015081299 | 6/2015 |
| WO | 2015095924 | 7/2015 |
| WO | 2015127143 | 8/2015 |
| WO | 2015127441 | 8/2015 |
| WO | 2016017997 | 2/2016 |

OTHER PUBLICATIONS

Invitation to Pay Additional Search Fees, dated Nov. 4, 2015, from corresponding International Application Serial No. PCT/US2015/048656.

International Search Report, dated Dec. 18, 2015, from corresponding International Application No. PCT/US2015/048662.

Written Opinion of the International Searching Authority, dated Dec. 18, 2015, from corresponding International Application No. PCT/US2015/048662.

Office Action, dated Dec. 29, 2016, from corresponding U.S. Appl. No. 14/610,589.

Phend, Crystal, "Calorie Intake Rises as Sleep Time Drops," Medpage Today, Medpage Today, LLC, Mar. 15, 2012, Web Dec. 19, 2016, http://www.medpagetoday.com/cardiology/prevention/31663.

International Search Report, dated Jan. 21, 2016, from corresponding International Application No. PCT/US2015/048612.

(56) References Cited

OTHER PUBLICATIONS

Written Opinion of the International Searching Authority, dated Jan. 21, 2016, from corresponding International Application No. PCT/US2015/048612.
International Search Report, dated Jan. 21, 2016, from corresponding International Application No. PCT/US2015/048656.
Written Opinion of the International Searching Authority, dated Jan. 21, 2016, from corresponding International Application No. PCT/US2015/048656.
International Search Report, dated Jun. 2, 2016, from corresponding International Application No. PCT/US2016/015705.
Invitation to Pay Additional Search Fees, dated Apr. 1, 2016, from corresponding International Application Serial No. PCT/US2016/015705.
Written Opinion of the International Searching Authority, dated Jun. 2, 2016, from corresponding International Application No. PCT/US2016/015705.
Final Office Action, dated Sep. 26, 2016, from corresponding U.S. Appl. No. 14/610,628.
Office Action, dated Mar. 8, 2016, from corresponding U.S. Appl. No. 14/610,628.
Office Action, dated Jul. 22, 2016, from corresponding U.S. Appl. No. 14/506,249.
Office Action, dated Aug. 19, 2016, from corresponding U.S. Appl. No. 14/578,039.
Office Action, dated Sep. 2, 2016, from corresponding U.S. Appl. No. 14/588,122.
Restriction Requirement, dated Nov. 10, 2016, from corresponding U.S. Appl. No. 14/846,401.
Final Office Action, dated Dec. 15, 2016, from corresponding U.S. Appl. No. 14/506,249.
Maria S. Redin, "Marathon Man", Article Jun. 15, 1998, MIT Media Laboratory.
Richard M. Satava, et al., "The Physiologic Cipher at Altitude: Telemedicine and Real-Time Monitoring of Climbers on Mount Everest", Telemedicine Journal and e-Health, vol. 6, No. 3, 2000, Mary Ann Liebert, Inc.
Michael Franco, Tzoa wearable turns you into a walking air-quality sensor, Dec. 9, 2014, CNET, https://www.cnet.com/news/tzoa-wearable-turns-you-into-a-walking-air-quality-sensor/.
Notice of Allowance, dated Feb. 28, 2017, from corresponding U.S. Appl. No. 14/588,122.
Office Action, dated Feb. 10, 2017, from corresponding U.S. Appl. No. 14/846,401.
Office Action, dated Mar. 3, 2017, from corresponding U.S. Appl. No. 14/610,628.
Ted Burnham, Wearable Air Quality Sensor: Tzoa, Jan. 5, 2015, Postscapes, http://www.postscapes.com/wearable-air-quality-sensor-tzoa/.
International Preliminary Report on Patentability, dated Mar. 16, 2017, from corresponding International Application No. PCT/US2015/048612.
International Preliminary Report on Patentability, dated Mar. 16, 2017, from corresponding International Application No. PCT/US2015/048656.
International Preliminary Report on Patentability, dated Mar. 16, 2017, from corresponding International Application No. PCT/US2015/048662.
Final Office Action, dated Jun. 30, 2017, from corresponding U.S. Appl. No. 14/610,589.
Shankland, Stephen, "Google's electronic eyewear get 'OK Glass' voice commands", Feb. 20, 2013, Cnet.com, https://www.cnet.com/news/googles-electronic-eyewear-gets-ok-glass-voice-commands/.
Office Action, dated Jun. 29, 2017, from corresponding U.S. Appl. No. 15/489,147.
Final Office Action, dated Jul. 10, 2017, from corresponding U.S. Appl. No. 14/846,401.
Final Office Action, dated May 23, 2017, from corresponding U.S. Appl. No. 14/578,039.
Office Action, dated Jun. 27, 2017, from corresponding U.S. Appl. No. 15/060,333.

* cited by examiner

SYSTEM FOR MONITORING INDIVIDUALS AS THEY AGE IN PLACE

CROSS-REFERENCE TO RELATED APPLICATION

This application claims the benefit of U.S. Provisional Patent Application No. 62/046,406, filed Sep. 5, 2014, and entitled, "Wearable Health Computer Apparatus, Systems, and Related Methods," which is hereby incorporated herein by reference in its entirety.

BACKGROUND

Being able to monitor elderly individuals who live independently at home has become increasingly important due, in part, to the high cost of elder care facilities. Accordingly, there is a need for improved systems and methods for monitoring the activities and wellbeing of elderly individuals living at home. There is a similar need for monitoring the activities and wellbeing of individuals with special needs living outside of an institutional setting. Various embodiments of the present systems and methods recognize and address the foregoing considerations, and others, of prior art systems and methods.

SUMMARY OF THE VARIOUS EMBODIMENTS

A computer-implemented method of monitoring the wellbeing of an individual according to various embodiments comprises the steps of: (1) providing a user with computerized eyewear comprising at least one sensor for monitoring the motion of the user; (2) receiving data generated by the at least one sensor; (3) determining the user's movements using the received data; (4) comparing the user's movements to previously established one or more movement patterns for the user; (5) determining whether one or more inconsistencies exist between the current user's movements and the previously-established one or more movement patterns; and (6) at least partially in response to determining that such one or more inconsistencies exist, notifying a recipient selected from a group consisting of: the user and/or a third party of the detected one or more inconsistencies.

A computer-implemented method of monitoring the wellbeing of an individual according to further embodiments comprises the steps of: (1) providing a user with a computerized wearable device comprising at least one sensor for monitoring actions taken by a user; (2) receiving a medicine regime associated with the user; (3) receiving data generated by the at least of the wearable device's sensors; (4) analyzing the received data generated by the at least one sensor to determine: (a) the type of medicine taken by the wearer; (b) the time the medicine is taken by the wearer; and/or (c) the dose of medicine taken by the wearer; (5) comparing the medicine regime for the user to the determined one or more of the type of medicine taken by the wearer, the time the medicine is taken by the wearer, and/or dose of medicine taken by the wearer; (6) detecting one or more inconsistencies between the medicine regime associated with the user and the determined one or more of the type of medicine taken by the user, the time the medicine is taken by the user, and/or the dose of medicine taken by the user; (7) notifying the user and/or third party of the detected inconsistencies.

BRIEF DESCRIPTION OF THE DRAWINGS

Various embodiments of systems and methods for assessing a user's activities and movements are described below. In the course of this description, reference will be made to the accompanying drawings, which are not necessarily drawn to scale and wherein.

DETAILED DESCRIPTION OF SOME EMBODIMENTS

Various embodiments will now be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

A wearable health monitoring system, according to various embodiments, may include a suitable wearable device that is configured to monitor one or more movements, activities, and/or health attributes of a wearer (e.g., user). Suitable wearable devices may include, for example: (1) pair of eyewear (e.g., goggles or eyeglasses); (2) one or more contact lenses; (3) a wristwatch; (4) an article of clothing (e.g., such as a suitable shirt, pair of pants, undergarment, compression sleeve, etc.); (5) footwear; (6) a hat; (7) a helmet; (8) an adhesive strip or other tag that may be selectively attached to an individual or the individual's clothing; (9) a computing device that is embedded into a portion of an individual's body (e.g., under the individual's skin, or within a medical device, such as a pacemaker); (10) an orthopedic cast, or (11) any other suitable wearable item. In a particular example, a wearable health monitoring system embodied as a pair of eyewear may enable the system to monitor what an individual is sensing (e.g., touching, seeing, hearing, smelling, and/or tasting) based at least in part on a proximity of the eyewear to the wearer's sensory systems (e.g., skin, eyes, mouth, ears, nose) when worn by the wearer.

In various embodiments, the system comprises one or more sensors that are configured to determine one or more current physical attributes of the wearer (e.g., heart rate, brain wave activity, movement, body temperature, blood pressure, oxygen saturation level, etc . . . ). The one or more sensors may include, for example: (1) one or more heart rate monitors; (2) one or more electrocardiograms (EKG); (3), one or more electroencephalograms (EEG); (4) one or more pedometers; (5) one or more thermometers; (6) one or more transdermal transmitter sensors; (7) one or more front-facing cameras; (8) one or more eye-facing cameras; (9) one or more microphones; (10) one or more accelerometers; (11) one or more blood pressure sensors; (12) one or more pulse oximeters; (13) one or more respiratory rate sensors; (14) one or more blood alcohol concentration (BAC) sensors; (15) one or more near-field communication sensors; (16) one or more motion sensors; (17) one or more gyroscopes; (18) one or more geomagnetic sensors; (19) one or more global positioning system sensors; (20) one or more impact sensors; and/or (21) any other suitable one or more sensors.

In particular embodiments, the system is configured to gather data, for example, using the one or more sensors, about the wearer (e.g., such as the wearer's body temperature, balance, heart rate, level of physical activity, diet (e.g., food recently eaten), compliance with a prescribed medical regimen (e.g., medications recently taken), position, movements (e.g., body movements, facial muscle movements), location, distance traveled, etc.). In various embodiments, the system is configured to, for example: (1) store the gathered data associated with the user; (2) provide the data to one or more medical professionals, for example, to aid in the diagnosis and/or treatment of the user; (3) use the data to predict one or more medical issues with the user (e.g., the illness or death of the user); and/or (4) take any other suitable action based at least in part on the gathered data.

In a particular implementation, the system's wearable device is a pair of computerized eyewear that comprises one or more sensors for monitoring one or more day-to-day activities of an elderly individual as they "age in place" (e.g., they live in a non-institutional setting). In particular embodiments, the one or more sensors are coupled to (e.g., connected to, embedded in, etc.) the pair of glasses, which may be, for example, a pair of computerized or non-computerized eyeglasses. In particular embodiments, the individual is a senior citizen who lives at least substantially independently.

In particular embodiments, the wearable computing device comprises one or more location sensors (e.g., geomagnetic sensors, etc.), motion sensors (e.g., accelerometers, gyroscopes, magnetic sensors, pressure sensors, etc.), and/or impact sensors that are adapted to sense the movement and location of the individual. In various embodiments, the wearable device is adapted to facilitate the transmission of this movement information to a remote computing device (e.g., a handheld computing device, an automated dialing device, a central server, or any other suitable smart device that may, in various embodiments, contain a wireless communications device that can connect to the wearable computing device) that analyzes the information to determine whether the individual's movement patterns are consistent with the individual's typical (e.g., past) movement patterns. If the movement patterns are inconsistent with the individual's typical movement patterns, the system may, for example, generate and transmit an alert to a third party (e.g., a physician, relative of the individual, other caretaker, police, etc.) informing the third party of the irregularities in the individual's movement. The third party may then, for example, check on the individual to make sure that the individual does not require assistance.

In further embodiments, the wearable device may be adapted, for example, to monitor: (1) an individual's compliance with a prescribed treatment plan (e.g., compliance with a medication schedule); (2) an individual's compliance with a diet; and/or (3) whether an individual leaves a prescribed area defined by a geo-fence (e.g., a virtual fence). The system may do this, for example, by using any suitable sensors (e.g., location sensors, cameras, etc . . . ) associated with the wearable device.

Exemplary Technical Platforms

As will be appreciated by one skilled in the relevant field, the present systems and methods may be, for example, embodied as a computer system, a method, or a computer program product. Accordingly, various embodiments may be entirely hardware or a combination of hardware and software. Furthermore, particular embodiments may take the form of a computer program product stored on a computer-readable storage medium having computer-readable instructions (e.g., software) embodied in the storage medium. Various embodiments may also take the form of Internet-implemented computer software. Any suitable computer-readable storage medium may be utilized including, for example, hard disks, compact disks, DVDs, optical storage devices, and/or magnetic storage devices.

Various embodiments are described below with reference to block diagram and flowchart illustrations of methods, apparatuses, (e.g., systems), and computer program products. It should be understood that each block of the block diagrams and flowchart illustrations, and combinations of blocks in the block diagrams and flowchart illustrations, respectively, can be implemented by a computer executing computer program instructions. These computer program instructions may be loaded onto a general purpose computer, a special purpose computer, or other programmable data processing apparatus that can direct a computer or other programmable data processing apparatus to function in a particular manner such that the instructions stored in the computer-readable memory produce an article of manufacture that is configured for implementing the functions specified in the flowchart block or blocks.

The computer instructions may execute entirely on the user's computer, partly on the user's computer, as a stand-alone software package, partly on a user's computer and partly on a remote computer, or entirely on the remote computer or server. In the latter scenario, the remote computer may be connected to the user's computer through any type of network, including but not limited to: (1) a local area network (LAN); (2) a wide area network (WAN); (3) a cellular network; or (4) the connection may be made to an external computer (for example, through the Internet using an Internet Service Provider).

These computer program instructions may also be stored in a computer-readable memory that can direct a computer or other programmable data processing apparatus to function in a particular manner such that the instructions stored in the computer-readable memory produce an article of manufacture that is configured for implementing the function specified in the flowchart block or blocks. The computer program instructions may also be loaded onto a computer or other programmable data processing apparatus to cause a series of operational steps to be performed on the computer or other programmable apparatus to produce a computer-implemented process (e.g., method) such that the instructions that execute on the computer or other programmable apparatus provide steps for implementing the functions specified in the flowchart block or blocks.

Example System Architecture

Figure 1:
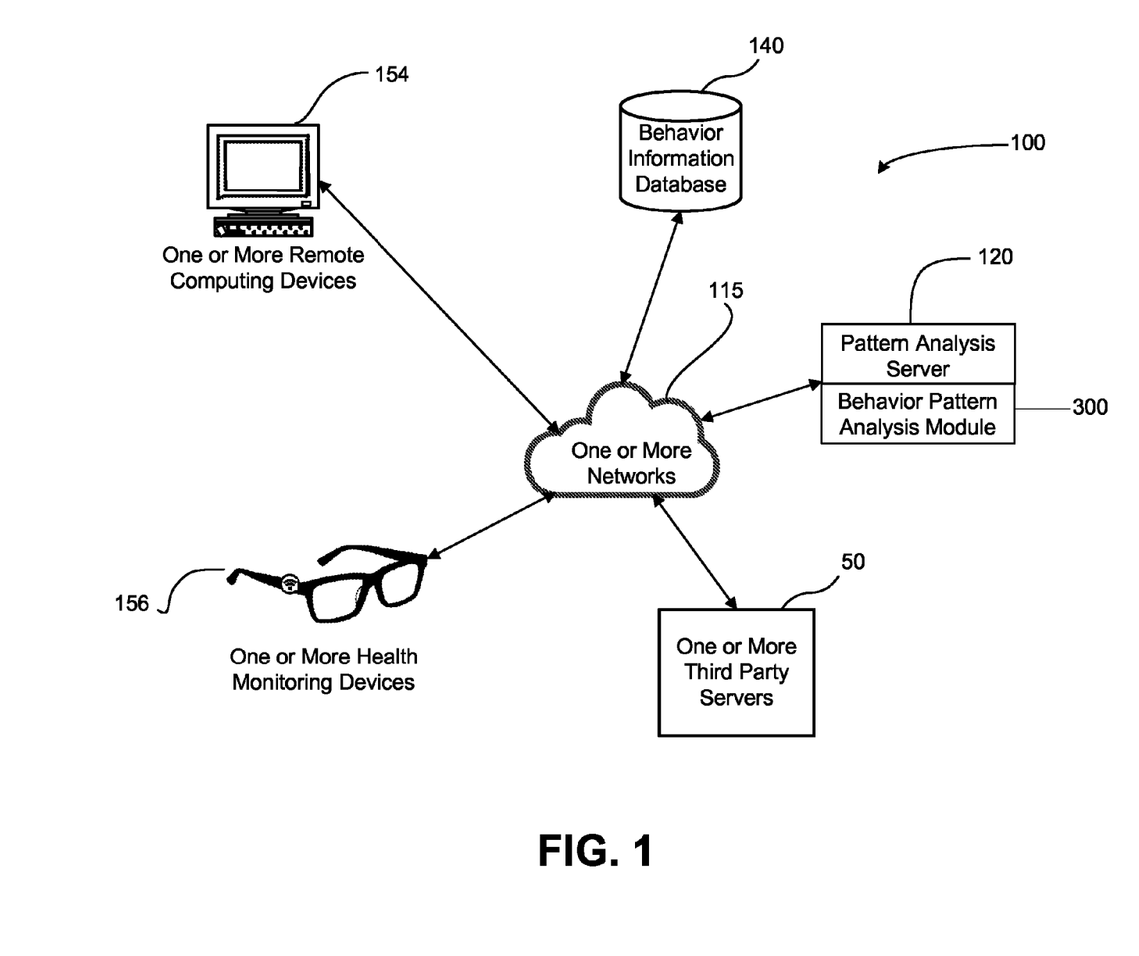
FIG. 1 is a block diagram of a Behavior Pattern Analysis System in accordance with an embodiment of the present system.

FIG. 1 is a block diagram of a Behavior Pattern Analysis System 100 according to particular embodiments. As may be understood from this figure, the Behavior Pattern Analysis System 100 includes One or More Networks 115, One or More Third Party Servers 50, a Pattern Analysis Server 120 that includes a Behavior Pattern Analysis Module 300, a Movement Information Database 140, One or More Remote Computing Devices 154 (e.g., such as a smart phone, a tablet computer, a wearable computing device, a laptop computer, a desktop computer, a Bluetooth device, an automated dialing apparatus, etc.), and One or More Wearable Health Monitoring Devices 156, which may, for example, be embodied as one or more of eyewear, headwear, clothing, a watch, a hat, a helmet, a cast, an adhesive bandage, a piece of jewelry (e.g., a ring, earring, necklace, bracelet, etc.), or any other suitable wearable device. In particular embodiments, the one or more computer networks 115 facilitate communication between the One or More Third Party Servers 50, the Pattern Analysis Server 120, the Movement Information Database 140, the One or More Remote Computing Devices 154, and the one or more Health Monitoring Devices 156.

The one or more networks 115 may include any of a variety of types of wired or wireless computer networks such as the Internet, a private intranet, a mesh network, a public switch telephone network (PSTN), or any other type of network (e.g., a network that uses Bluetooth or near field communications to facilitate communication between computing devices). The communication link between the One or More Remote Computing Devices 154 and the Pattern Analysis Server 120 may be, for example, implemented via a Local Area Network (LAN) or via the Internet.

Figure 2:
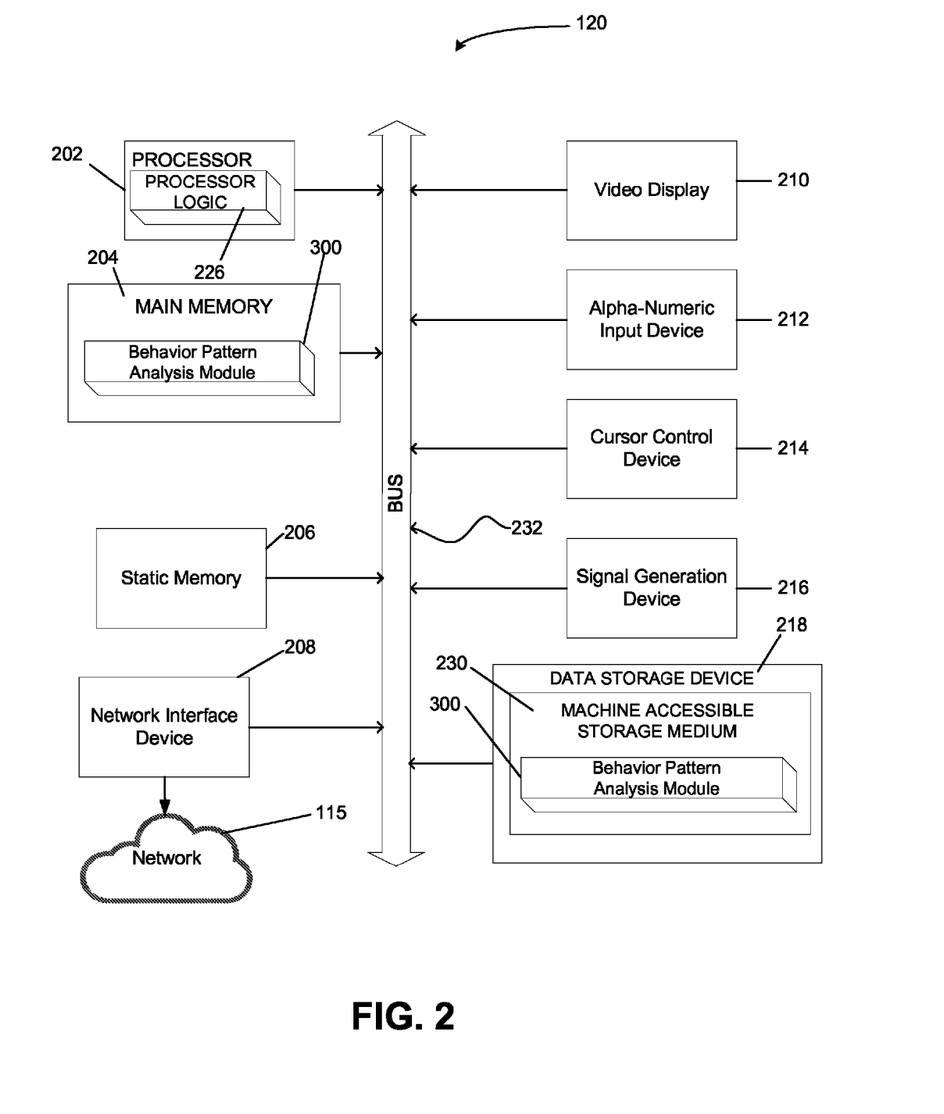
FIG. 2 is a block diagram of the Pattern Analysis Server of FIG. 1.

FIG. 2 illustrates a diagrammatic representation of the architecture for the Pattern Analysis Server 120 that may be used within the Behavior Pattern Analysis System 100. It should be understood that the computer architecture shown in FIG. 2 may also represent the computer architecture for any one of the One or More Remote Computing Devices 154, one or more Third Party Servers 50, and One or More Health Monitoring Devices 156 shown in FIG. 1. In particular embodiments, the Pattern Analysis Server 120 may be suitable for use as a computer within the context of the Behavior Pattern Analysis System 100 that is configured for monitoring the behavior (e.g., movements, location, eating and sleeping habits) of the wearer.

In particular embodiments, the Pattern Analysis Server 120 may be connected (e.g., networked) to other computing devices in a LAN, an intranet, an extranet, and/or the Internet as shown in FIG. 1. As noted above, the Pattern Analysis Server 120 may operate in the capacity of a server or a client computing device in a client-server network environment, or as a peer computing device in a peer-to-peer (or distributed) network environment. The Pattern Analysis Server 120 may be a desktop personal computing device (PC), a tablet PC, a set-top box (STB), a Personal Digital Assistant (PDA), a cellular telephone, a web appliance, a network router, a switch or bridge, or any other computing device capable of executing a set of instructions (sequential or otherwise) that specify actions to be taken by that computing device. Further, while only a single computing device is illustrated, the term "computing device" shall also be interpreted to include any collection of computing devices that individually or jointly execute a set (or multiple sets) of instructions to perform any one or more of the methodologies discussed herein.

An exemplary Pattern Analysis Server 120 includes a processing device 202, a main memory 204 (e.g., read-only memory (ROM), flash memory, dynamic random access memory (DRAM) such as synchronous DRAM (SDRAM) or Rambus DRAM (RDRAM), etc.), a static memory 206 (e.g., flash memory, static random access memory (SRAM), etc.), and a data storage device 218, which communicate with each other via a bus 232.

The processing device 202 represents one or more general-purpose or specific processing devices such as a microprocessor, a central processing unit (CPU), or the like. More particularly, the processing device 202 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. The processing device 202 may also be one or more special-purpose processing devices such as an application specific integrated circuit (ASIC), a field programmable gate array (FPGA), a digital signal processor (DSP), network processor, or the like. The processing device 202 may be configured to execute processing logic 226 for performing various operations and steps discussed herein.

The Pattern Analysis Server 120 may further include a network interface device 208. The Pattern Analysis Server 120 may also include a video display unit 210 (e.g., a liquid crystal display (LCD) or a cathode ray tube (CRT)), an alpha-numeric input device 212 (e.g., a keyboard), a cursor control device 214 (e.g., a mouse), and a signal generation device 216 (e.g., a speaker).

The data storage device 218 may include a non-transitory computing device-accessible storage medium 230 (also known as a non-transitory computing device-readable storage medium or a non-transitory computing device-readable medium) on which is stored one or more sets of instructions (e.g., the Behavior Pattern Analysis Module 300) embodying any one or more of the methodologies or functions described herein. The one or more sets of instructions may also reside, completely or at least partially, within the main memory 204 and/or within the processing device 202 during execution thereof by the Pattern Analysis Server 120—the main memory 204 and the processing device 202 also constituting computing device-accessible storage media. The one or more sets of instructions may further be transmitted or received over a network 115 via a network interface device 208.

While the computing device-accessible storage medium 230 is shown in an exemplary embodiment to be a single medium, the term "computing device-accessible storage medium" should be understood to include a single medium or multiple media (e.g., a centralized or distributed database, and/or associated caches and servers) that store the one or more sets of instructions. The term "computing device-accessible storage medium" should also be understood to include any medium that is capable of storing, encoding, or carrying a set of instructions for execution by the computing device and that causes the computing device to include any one or more of the methodologies of the present invention. The term "computing device-accessible storage medium" should accordingly be understood to include, but not be limited to, solid-state memories, optical and magnetic media, etc.

Exemplary System Platform

As noted above, a system, according to various embodiments, is adapted to monitor one or more patterns of behavior and/or one or more locations of a user of a wearable device. Various aspects of the system's functionality may be executed by certain system modules, including the Behavior Pattern Analysis Module 300. The Behavior Pattern Analysis Module 300 is discussed in greater detail below.

Behavior Pattern Analysis Module

Figure 3:
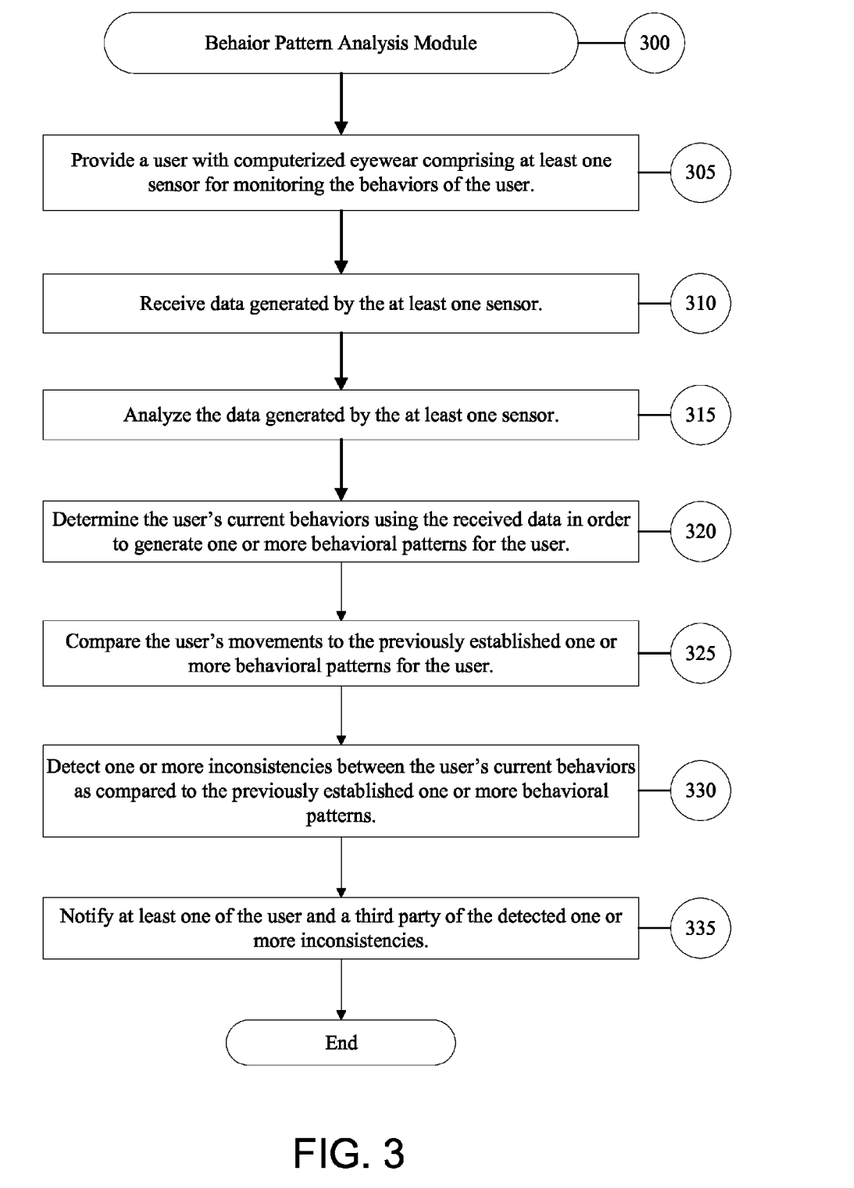
FIG. 3 is a flowchart that generally illustrates various steps executed by a Behavior Pattern Analysis Module according to a particular embodiment.

FIG. 3A is a flow chart of operations performed by an exemplary Behavior Pattern Analysis Module 300, which may, for example, run on the Pattern Analysis Server 120, or any suitable computing device (such as the One or More Health Monitoring Devices 156, a handheld computing device coupled to communicate with the One or More Health Monitoring Devices 156 or a suitable mobile computing device). In particular embodiments, the Behavior Pattern Analysis Module 300 may assess a user's behavior and determine the user's location to provide this information to the user or to a third party.

The system begins, in various embodiments, at Step 305 by providing a user with computerized eyewear comprising at least one sensor for monitoring one or more behaviors of the user and/or any suitable attributes of the user. In various embodiments, the at least one sensor may include a location sensor (e.g., a GPS unit), an accelerometer, a heart rate monitor, one or more electrocardiogram (EKG), an electroencephalogram (EEG), a pedometer, a thermometer, a front-facing camera, an eye-facing camera, a microphone, an accelerometer, a blood pressure sensor, a pulse oximeter, a near-field communication sensor, a motion sensor, a gyroscope, a geomagnetic sensor, an impact sensor, and/or any other suitable sensor. In particular embodiments, the computerized eyewear further comprises: a motion sensor, an accelerometer, a GPS unit, a gyroscope, and/or a front-facing camera.

In particular embodiments, the sensors may be coupled to the eyewear in any suitable way. For example, in various embodiments, the sensors may be physically embedded into, or otherwise coupled to the eyewear. In some embodiments, the sensors may be positioned: (1) along the brow bar of the eyewear; (2) along the temples of the eyewear; (3) adjacent the lenses of the eyewear; and/or (4) in any other suitable location.

In particular embodiments: (1) the sensors are coupled to a wireless (e.g., Bluetooth, near-field communications, Wi-Fi, etc.) device that is configured to transmit one or more signals obtained from the one or more sensors to a handheld wireless device (e.g., a smartphone, a tablet, an automated dialing device, etc.); and (2) the step of receiving one or more signals from the one or more sensors further comprises receiving the one or more signals from the wireless handheld device via the Internet. In particular embodiments, one or more of the sensors may be selectively detachable from the eyewear, or other wearable device. For example, if a user does not need the temperature sensor, the temperature sensor may be selectively removed from the eyewear and stored for future use.

At Step 310, the system receives data generated by the at least one sensor. In particular embodiments, the data generated by the at least one sensor may include data for a heart rate, a heart rhythm or electrical activity, a brain wave activity, a distance traveled, a temperature, an image, a sound, a speed traveled, a blood pressure, an oxygen saturation level, a near-field communication, a motion, an orientation, a geomagnetic field, a global position, an impact, a medicine regime, or any other suitable data.

In various embodiments, the system may receive the data substantially automatically after the sensor generates the data. In some embodiments, the system may receive the data periodically (e.g., by the second, by the minute, hourly, daily, etc.). For example, the system may receive the data every thirty seconds throughout the day. In other embodiments, the system may receive the data after receiving an indication from the user or a third party that the system should receive the data. For instance, the user may speak a voice command to the wearable device requesting that the device track the user's steps taken. In various embodiments, the system may receive an indication from the user or a third party of when to have the system receive the data. For example, the system may receive an indication from the third party to have the system receive global positioning data at 8:00 a.m. and at 2:00 p.m.

In particular embodiments, the system may receive an indication from the user or a third party to have particular data received from a particular sensor at the same time that the system receives second particular data from a second particular sensor. For example, when the system receives data that indicates that the user's speed has increased, the system may at least partially in response to receiving the increased speed data, also obtain global position data of the user. In particular embodiments, the system may receive behavior data during a predefined time period. For instance, the system may receive behavior data for the user during a predefined time period when the user should not be moving (e.g., 11:00 p.m. through 7:00 a.m. because the user should be sleeping). In various embodiments, the system may receive the data when a sensor detects movement of the user. For example, the system may receive data from the global positioning system sensor when the accelerometer or the gyroscope detects movement of the user.

In other embodiments, the data generated by the at least one sensor may be whether the user experiences one of sudden acceleration and sudden impact. In still other embodiments, the data generated by the at least one sensor may be a heartbeat and whether the user is breathing. In yet other embodiments, the data generated by the at least one sensor may be a medicine regime associated with the user. For instance, the user or the user's physician may manually input a medicine regime into the system by stating the name of the medicine while the user or the user's physician requests that the front-facing camera capture an image of the medicine and the medicine bottle. In some embodiments, the received data generated by the at least one sensor may be one or more images captured by the forward facing camera. In other embodiments, the received data generated by the at least one sensor may be the level of one or more medicines in the user's bloodstream.

In various embodiments, the system may receive data from a single sensor. In other embodiments, the system may receive data from all of the sensors. In yet other embodiments, the system may receive multiple data from each of the sensors. In various embodiments, the system may be configured to receive first data from a first sensor at the same time that it receives second data from a second sensor. For example, the system may be configured to receive a global position from the global positioning system sensor at the same time that it receives impact data from the impact sensor.

In particular embodiments, the system may store the received data. In various embodiments, the system may store the received data substantially automatically after receiving the data. In other embodiments, the system may store the received data after receiving manual input from the user or a third party requesting that the system store the data. In various embodiments, the system may store the received data for a specified period of time. For instance, the system may store the received data for a day, a month, a year, etc., in the Behavior Information Database 140. In some embodiments, the system may store the received data on any suitable server, database, or device. In other embodiments, the system may store the received data on the Pattern Analysis Server 120. In still other embodiments, the system may store the received data in an account associated with the user. In various embodiments, the system may store the received data with a timestamp of when the data was received.

At Step 315, the system analyzes the data generated by the at least one sensor. In various embodiments, the system analyzes the data generated by the at least one sensor substantially automatically after receiving the generated data. In various embodiments, the system may analyze the data periodically (e.g., by the second, by the minute, hourly, daily, etc.). For example, the system may analyze the data every thirty seconds throughout the day. In other embodiments, the system may analyze the data after receiving an indication from the user or a third party that the system should analyze data. For instance, the user may speak a voice command to the wearable device requesting that the device analyze the user's steps taken. In various embodiments, the system may receive an indication from the user or a third party of when to have the system analyze the data. For example, the system may receive an indication from the third party to have the system analyze global positioning data at 8:00 a.m. and at 2:00 p.m.

In other embodiments, the system may analyze the data to determine one or more of (1) the type of medicine taken by the user; (2) the time the medicine is taken by the user; and (3) the dose of medicine taken by the user. In still other embodiments, the step of analyzing the received data further comprises detecting one or more pills in the one or more images, comparing the one or more detected pills found in the one or more images to known images of pills stored in a database, identifying the one or more pills by matching the one or more pills from the one or more images to the known images of pills stored in the database, and detecting the time that the image was taken. In various embodiments, the system analyzes the level of the one or more medicines in the user's bloodstream.

Then, at Step 320, the system determines the user's current movements using the received data in order to generate one or more movement patterns for the user. In various embodiments, the system determines the user's current movements substantially automatically after receiving the data. In various embodiments, the system may determine the user's current movements periodically (e.g., by the second, by the minute, hourly, daily, etc.). For example, the system may determine the user's current movements every thirty seconds throughout the day. In other embodiments, the system may determine the user's current movements after receiving an indication from the user or a third party that the system should analyze data. For instance, the user may speak a voice command to the wearable device requesting that the device analyze the user's steps taken. In various embodiments, the system may receive an indication from the user or a third party of when to have the system analyze the data. For example, the system may receive an indication from the third party to have the system analyze global positioning data at 8:00 a.m. and at 2:00 p.m.

In various embodiments, the system determines the user's current movements by calculating the number of steps taken by the user in a particular day. In some embodiments, the system determines the user's current movements by tracking the distance traveled by the user for a particular day. In other embodiments, the system determines the user's current movements by capturing a series of images from the front-facing camera throughout the day. In still other embodiments, the system determines the user's current movements by tracking the orientation of the user using the gyroscope. In particular embodiments, the current movements of the user may include actions such as lying down, falling, wandering, sitting, standing, walking, running, convulsing, shaking, balancing, etc.

In various embodiments, the user's current movements may include the user's current location. For example, the user's current location may be an address, a geographic area, an intersection, a bus stop, a building, or any other suitable definable location. In other embodiments, the user's current movements may help to indicate the user's current status (e.g., asleep, awake, conscious, unconscious, alive, deceased, stable, good, fair, serious, critical, injured, distressed, etc.). In some embodiments, the user's current behaviors may include compliance with prescribed treatment regimes. For instance, the user's current behaviors may include that the user has not been complying with prescribed treatment regimes as captured through the front-facing camera of the user not taking prescribed medicine.

In various embodiments, the system tracks current movements, current location, current status, and current compliance to generate one or more movement patterns, location patterns, status patterns, and compliance patterns. In some embodiments, the system generates the one or more patterns substantially automatically after the system determines the user's current movements, location, status, and compliance. In some embodiments, the system may generate the patterns periodically (e.g., by the second, by the minute, hourly, daily, weekly, monthly, etc.). For example, the system may generate a movement pattern for each month. In other embodiments, the system may generate the pattern after receiving an indication from the user or a third party that the system should generate the pattern. For instance, the user may speak a voice command to the wearable device requesting that the device generate a pattern for the number of steps taken by the user for a typical day. In various embodiments, the system may receive an indication from the user or a third party of when to have the system generate the patterns. For example, the system may receive an indication from the third party to have the system generate a location pattern for the location of the user at 8:00 a.m. and at 2:00 p.m. for the previous month.

In various embodiments, the movement patterns may include one or more typical movements made by the user. For example, the movement pattern may include that the user gets out of bed every morning. In particular embodiments, the location patterns may include one or more typical locations of the user. For instance, the location pattern may include that the user is at a first particular address in the morning, at a second particular address during the day, and at the first particular address at night. In some embodiments, the status patterns may include one or more typical statuses of the user. In example, the status pattern may include that the user is awake from 7:00 a.m. until 11:00 p.m. and asleep from 11:00 p.m. until 7:00 a.m. In other embodiments, the compliance patterns may include one or more typical compliance schedules of the user. For example, the compliance pattern may include that the user is prescribed a medicine that the user takes every day in the morning with food. In yet other embodiments, the medicine regime patterns may include one or more typical medicine regimes for the user. For instance, the medicine regime pattern may include that the user takes a particular yellow pill, a particular white pill, and a particular pink pill in the evening with food. In various embodiments, the system may include one or more typical levels of one or more medicines in the user's bloodstream. For example, the typical level of a particular medicine in the user's bloodstream may be a certain volume at a particular period of time.

In particular embodiments, the system may store the generated patterns in an account associated with the user. In some embodiments, the generated patterns may be accessible by the user or a third party. For instance, the generated patterns may be diagramed in a chart that is accessible from the wearable device or from a computing device by the user's physician. In various embodiments, the system may store the generated patterns in the Behavior Information Database 140. In particular embodiments, the system may store information in the Behavior Information Database 140 regarding past movement patterns associated with the user (e.g., when the user goes into different rooms in the user's house, when the user eats, when the user takes a walk, the destinations along the walk, etc.). In some embodiments, the system may store information in the Behavior Information Database 140 regarding the user's sleep patterns. In other embodiments, the system may store information in the Behavior Information Database 140 regarding geo-fences associated with the user. In still other embodiments, the system may store information in the Behavior Information Database 140 regarding deviations to the user's typical behavior (e.g., movement) patterns.

At Step 325, the system compares the user's behaviors (e.g., movements) to the previously established one or more patterns for the user. In some embodiments, the system compares the user's movement to the previously established one or more movement patterns for the user substantially automatically after the system receives the user's current movements. In some embodiments, the system may compare the user's movement to the previously established one or more movement patterns periodically (e.g., by the second, by the minute, hourly, daily, weekly, monthly, etc.). For example, the system may compare the user's current movement to the previously established one or more movement patterns every thirty minutes throughout the day. In other embodiments, the system may compare the user's movement to the previously established one or more movement patterns after receiving an indication from the user or a third party that the system should compare the user's movement to the previously established movement pattern. For instance, the user may speak a voice command to the wearable device requesting that the device compare the user's movements for the current day to a movement pattern established the previous month. In various embodiments, the system may receive an indication from the user or a third party of when to have the system compare the user's movements to the one or more patterns. For example, the system may receive an indication from the third party to have the system compare the user's current location to a location pattern for the location of the user at 8:00 a.m. and at 2:00 p.m. on a typical day.

In some embodiments, the system may compare the user's movements to a previously established movement pattern by calculating the number of steps taken by the user in the particular day to a predetermined average number of steps taken by the user in a day. In various embodiments, the system may compare the user's location to a previously established location pattern by determining the average location of the user at a particular time of day. In other embodiments, the system may compare the user's status to a previously established status pattern by determining the user's average status at particular times of day.

In still other embodiments, the system may compare the user's compliance with a prescribed treatment regime by determining the user's average compliance with the prescribed treatment regime for a particular day. In yet other embodiments, the system may compare the one or more of the type of medicine taken; the time the medicine is taken; and the dose of the medicine taken to the stored medicine regime for the user. In various embodiments, the system may compare the level of one or more medicines in the user's bloodstream by determining the average level of the one or more medicines in the user's bloodstream at particular times of day.

In particular embodiments, the system may store the comparisons in an account associated with the user. In some embodiments, the comparisons may be accessible by the user or a third party. For instance, the comparisons may be diagramed in a chart that is accessible from the wearable device or from a computing device by the user's physician.

Continuing to Step 330, the system detects one or more inconsistencies between the user's current movements as compared to the previously established one or more patterns. In other embodiments, the system does not detect one or more inconsistencies between the user's current movements as compared to the previously established one or more patterns. In various embodiments, the system may detect the one or more inconsistencies by determining that the user's current movements are inconsistent with the previously established patterns. In particular embodiments, the user's current movements may be inconsistent with previously established patterns based on the current movements being different from the established patterns by a particular percentage. For instance, where the user's movement patterns establish that the user walks a total of one mile a day, the system may determine that the user's current movement of walking ½ mile for the day is inconsistent with the user's previously established pattern of walking one mile a day because there is a difference of 50%.

In some embodiments, the user's current movements may be inconsistent with the previously established movement patterns based on the user's current movements not matching the previously established movement patterns. For instance, for the movement pattern that includes that the user gets out of bed every morning, where the system detects that the user does not get out of bed on a particular morning, the system may determine that the user's current movements are inconsistent with the previously established pattern.

In other embodiments, the user's current movements may be inconsistent with the previously established patterns based on the user's current location not matching the previously established location patterns. For example, for the location pattern that includes the user at a first particular address in the morning, at a second particular address during the day, and at the first particular address at night, where the system detects that the user was not at the second particular address during the day, the system may determine that the user's current movements are inconsistent with the previously established pattern.

In still other embodiments, the user's current movements may be inconsistent with the previously established patterns based on the user's current status not matching the previously established status patterns. For instance, for the status pattern that includes that the user is awake from 7:00 a.m. until 11:00 p.m. and asleep from 11:00 p.m. until 7:00 a.m., where the system detects that the user is asleep from 7:00 a.m. until 2:00 p.m., the system may determine that the user's current movements are inconsistent with the previously established pattern.

In yet other embodiments, the system may detect one or more inconsistencies between the medicine regime associated with the user and the determined one or more of the type of medicine taken by the user, the time the medicine is taken by the user, and the dose of medicine taken by the user. For instance, for a medicine regime that includes that the user takes a particular pill having a particular color (e.g., yellow), shape (e.g., triangular, square), and marking (e.g., the number 17) in the evening with food, where the system detects that the user did not take the particular yellow pill on a particular evening with food, the system may determine that the user's current movements are inconsistent with the previously established pattern.

In some embodiments, the system may detect one or more inconsistencies between the level of the one or more medicines in the user's bloodstream and the determined typical level of the one or more medicines in the user's bloodstream. For example, for a typical level of a particular medicine in the user's bloodstream that includes that the level is a certain volume at a particular period of time, where the system detects that the level of the medicine in the user's bloodstream is less than the typical level, the system may determine that the user's current movements are inconsistent with the previously established patterns.

At Step 335, the system notifies the user and/or a third party of the detected one or more inconsistencies. In particular embodiments, in addition to notifying at least one recipient selected from a group consisting of: the user and the third party, the system updates the user's account to note that a notification was sent. In various embodiments, the system notifies the user of the detected one or more inconsistencies. In some embodiments, the system notifies the third party of the detected one or more inconsistencies. In particular embodiments, the system may notify the user of the detected one or more inconsistencies by displaying an image on the lens of the eyewear, or on another display associated with the eyewear. In other embodiments, the system notifies the user of the one or more inconsistencies by communicating through a speaker to the user.

In various embodiments, the third party may be a relative of the user. In other embodiments, the third party may be a police department. In particular embodiments, the third party may be an ambulance service. In some embodiments, the third party may be a physician. In still other embodiments, the third party may be an independent living provider. In yet other embodiments, the third party may be a particular caregiver of the user.

In some embodiments, the system notifies the user and/or the third party of the one or more inconsistencies by sending a notification to the user's and/or the third party's mobile devices. In particular embodiments, the system notifies the user and/or the third party of the one or more inconsistencies by email or text message. In other embodiments, the system may notify the user and/or the third party of a single inconsistency substantially immediately after the system detects the inconsistency between the user's current movements as compared to the previously established one or more movement patterns. In yet other embodiments, the system may notify the user and/or the third party of all inconsistencies detected on a particular day at the end of that day.

In various embodiments, the system may notify the user and/or the third party of the one or more inconsistencies after a particular event. For example, the system may notify the user if the system determines that the calculated number of steps of the user for a particular day is less than a predetermined percentage of the predetermined average number of steps taken by the user in a day. In some embodiments, the system may notify the user and/or the third party of the one or more inconsistencies after a particular period of time. For instance, the system may notify the third party of an association one hour after the system detects one or more inconsistencies between the user's current movements as compared to the previously established one or more movement patterns. In still other embodiments, the system may notify the user of the one or more inconsistencies at a particular time of day. As an example, the system may notify the user of one or more inconsistencies between the user's current movements as compared to the previously established one or more movement patterns at the end of the day.

In various embodiments, at least partially in response to detecting whether the user moves during the predefined time period, the system may notify the user and/or third party if the user does not move during the predefined time period. In other embodiments, at least partially in response to detecting one of sudden acceleration and sudden impact (e.g., such as that associated with a fall), the system may notify user and/or the third party that the user experienced the one of sudden acceleration and sudden impact. In some embodiments, at least partially in response to not detecting one of a heartbeat or breathing associated with the user, the system may notify the user and/or the third party that the heartbeat and/or breathing of the user cannot be detected. This may indicate, for example, a medical emergency associated with the user or a malfunction of one or more system components.

In particular embodiments, the system may notify the user and/or the third party of detected inconsistencies between the user's current movements and the previously established movement patterns. In some embodiments, the system may notify the user and/or the third party of detected inconsistencies between the user's current location and the previously established location patterns. In other embodiments, the system may notify the user and/or the third party of detected inconsistencies between the user's current status and the previously established status patterns. In still other embodiments, the system may notify the user and/or the third party of detected inconsistencies between the user's current compliance and the previously established compliance patterns. In yet other embodiments, the system may notify the user and/or the third party of detected inconsistencies between the user's current medicine regime and the previously established medicine regime patterns. In various embodiments, the system may notify at least one recipient selected from a group consisting of: the user and the third party of detected inconsistencies between the user's current level of one or more medicines and the previously established typical one or more levels of medicine.

In particular embodiments, the system may notify the user and/or the third party of detected inconsistencies between the stored medicine regime and the one or more of the type of medicine taken, the time the medicine is taken, and the dose of medicine taken. In some embodiments, the system may notify at least one recipient selected from a group consisting of: the user and the third party if the user removes the wearable device for a predetermined period of time. In other embodiments, the system may notify the user and/or the third party if the user does not consume food for a predetermined period of time. In particular embodiments, the system may notify the user and/or the third party if the user does not consume liquids for a predetermined period of time. In various embodiments, the system may notify the user and/or the third party if the user's caloric intake is above or below a predetermined number of calories. In some embodiments, the system may notify the user and/or the third party if the user's oxygen levels fall below a predetermined threshold. In other embodiments, the system may notify the user and/or the third party if the user's blood sugar drops below a predetermined threshold.

In various embodiments, the system, when executing the Behavior Pattern Analysis Module 300, may omit particular steps, perform particular steps in an order other than the order presented above, or perform additional steps not discussed directly above.

Structure of the Eyewear

Figure 4:
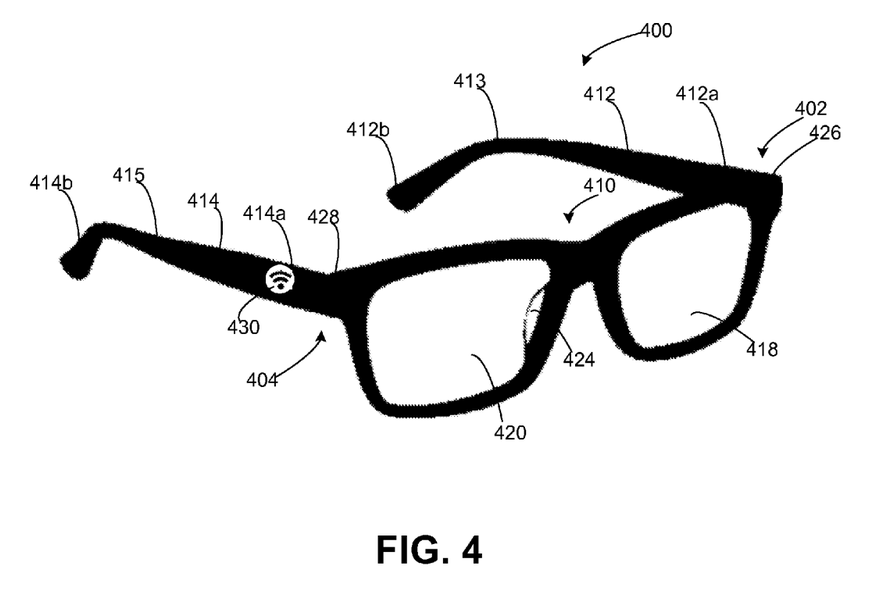
FIG. 4 is a perspective view of computerized eyewear according to a particular embodiment.

As shown in FIG. 4, eyewear 400, according to various embodiments, includes: (1) an eyewear frame 410; (2) a first temple 412; and (3) a second temple 414. These various components are discussed in more detail below. In various embodiments, the eyewear 400 may be used as the one or more health monitoring devices 156 shown in FIG. 1.

Eyewear Frame

Referring still to FIG. 4, eyewear 400, in various embodiments, includes any suitable eyewear frame 410 configured to support one or more lenses 418, 420. In the embodiment shown in this figure, the eyewear frame 410 has a first end 402 and a second end 404. The eyewear frame 410 may be made of any suitable material such as metal, ceramic, polymers or any combination thereof. In particular embodiments, the eyewear frame 410 is configured to support the first and second lenses 418, 420 about the full perimeter of the first and second lenses 418, 420. In other embodiments, the eyewear frame 410 may be configured to support the first and second lenses 418, 420 about only a portion of each respective lens. In various embodiments, the eyewear frame 410 is configured to support a number of lenses other than two lenses (e.g., a single lens, a plurality of lenses, etc.). In particular embodiments, the lenses 418, 420 may include prescription lenses, sunglass lenses, or any other suitable type of lens (e.g., reading lenses, non-prescription lenses), which may be formed from glass or polymers.

The eyewear frame 410 includes a first and second nose pad 422 (not shown in figures), 424, which may be configured to maintain the eyewear 400 adjacent the front of a wearer's face such that the lenses 418, 420 are positioned substantially in front of the wearer's eyes while the wearer is wearing the eyewear 400. In particular embodiments, the nose pads 422, 424 may comprise a material that is configured to be comfortable when worn by the wearer (e.g., rubber, etc.). In other embodiments, the nose pads may include any other suitable material (e.g., plastic, metal, etc.). In still other embodiments, the nose pads may be integrally formed with the frame 410.

The eyewear frame 410 includes a first and second hinge 426, 428 that attach the first and second temples 412, 414 to the frame first and second ends 402, 404, respectively. In various embodiments, the hinges may be formed by any suitable connection (e.g., tongue and groove, ball and socket, spring hinge, etc.). In particular embodiments, the first hinge 426 may be welded to, or integrally formed with, the frame 410 and the first temple 412 and the second hinge 428 may be welded to, or integrally formed with, the frame 410 and the second temple 414.

First and Second Temples

As shown in FIG. 4, the first temple 412, according to various embodiments, is rotatably connected to the frame 410 at a right angle to extend the first temple 412 substantially perpendicular, substantially parallel, or anywhere in between the right angle to the frame 410. The first temple 412 has a first and second end 412a, 412b. Proximate the first temple second end 412b, the first temple 412 includes an earpiece 413 configured to be supported by a wearer's ear. Similarly, the second temple 414, according to various embodiments, is rotatably connected to the frame 410 at a right angle to extend the second temple 414 substantially perpendicular, substantially parallel, or anywhere in between the right angle to the frame 410. The second temple 414 has a first and second end 414a, 414b. Proximate the second temple second end 414b, the second temple 414 includes an earpiece 415 configured to be supported by a wearer's ear.

Sensors

In various embodiments, the second temple 414 has one or more sensors 430 connected to the second temple 414. In various embodiments, the one or more sensors 430 may be coupled to the frame 410, the first and second temples 412, 414, the first and second lenses 418, 410, or any other portion of the eyewear 400 in any suitable way. For instance, the one or more sensors 430 may be embedded into the eyewear 400, coupled to the eyewear 400, and/or operatively coupled to the eyewear 400. In various embodiments, the one or more sensors may be formed at any point along the eyewear 400. For instance, a fingerprint reader may be disposed adjacent the first temple of the eyewear 400. In various embodiments, the one or more sensors may be formed in any shape. In addition, the one or more sensors may be formed on the inner (back) surface of the frame 410, the first and second temples 412, 414, the first and second lenses 418, 410, or any other portion of the eyewear 400. In other embodiments, the one or more sensors may be formed on the outer (front) surface of the frame 410, the first and second temples 412, 414, the first and second lenses 418, 410, or any other portion of the eyewear 400.

In various embodiments, the one or more sensors 430 that are coupled to the eyewear (or other wearable device) are adapted to detect one or more characteristics of the eyewear or a wearer of the eyewear, wherein the one or more characteristics of the wearer are associated with the wearer's identity. In various embodiments, the one or more sensors coupled to the eyewear or other health monitoring device may include, for example, one or more of the following: a near-field communication sensor, a gyroscope, a Bluetooth chip, a GPS unit, an RFID tag (passive or active), a fingerprint reader, an iris reader, a retinal scanner, a voice recognition sensor, a heart rate monitor, an electrocardiogram (EKG), an electroencephalogram (EEG), a pedometer, a thermometer, a front-facing camera, an eye-facing camera, a microphone, an accelerometer, a magnetometer, a blood pressure sensor, a pulse oximeter, a skin conductance response sensor, any suitable biometric reader, or any other suitable sensor. In some embodiments, the one or more sensors may include a unique shape, a unique code, or a unique design physically inscribed into the eyewear that may be readable by an individual or a remote computing device. In particular embodiments, the sensors coupled to the eyewear may include one or more electronic communications devices such as a near field communication sensor, a Bluetooth chip, an active RFID, and a GPS unit.

In various embodiments, the one or more sensors are coupled to a computing device that is associated with (e.g., embedded within, attached to) the eyewear or other wearable device. In particular embodiments, the eyewear or other wearable device comprises at least one processor, computer memory, suitable wireless communications components (e.g., a Bluetooth chip) and a power supply for powering the wearable device and/or the various sensors.

As noted above, the one or more sensors may be coupled to a Bluetooth device that is configured to transmit the one or more signals to a handheld wireless device, and the step of using the eyewear to confirm the identity of the wearer of the eyewear (discussed above in reference to Step 310) further comprises receiving the one or more signals from the wireless handheld device (e.g., via the Internet). In particular embodiments, one or more of the sensors may be detachable from the eyewear. For instance, if a wearer does not need a temperature sensor or other particular sensor, the sensor may be removed from the eyewear.

Exemplary User Experience

Independent Living of Elderly

In a particular example of a user using the Behavior Pattern Analysis Module 300, the user may put on the wearable device in the morning and continue to wear the device throughout the day. In various embodiments, the wearable device may be operatively coupled (e.g., via a suitable wireless or wired connection) to a smart phone, a laptop, a desktop computer, an automated dialing apparatus, or any other computing device that can receive signals from the wearable device and either transmit the signals to a central system (e.g., via a wireless or wired telephone network) or analyze the signals and make decisions based on the received signals (e.g., call for help, notify a loved one, etc.). During this time, the system will track the movements of the user using the motion sensor, the accelerometer, the global positioning sensor, the gyroscope, and the front-facing camera. In this example, the user may be an elderly or infirm person that desires to live independently, but the person requires monitoring for events that deviate from the person's normal routine. Thus, by wearing the wearable device throughout the day, the device is able to track the user's movements and create certain patterns based on these movements for the user. The system may then store these patterns in a database while continuing to track the user's movements. Where the system detects that the user has deviated from the previously established pattern, the system may notify the user's physician, for example directly from the wearable device, or via the connected smartphone, computer or the automated dialing apparatus. Such deviations from the previously established pattern may include that the user falls, that the user wanders beyond preset boundaries (e.g., defined by one or more geofences), that the user begins sleeping longer than usual, that the user stops moving, or any other deviation from a previously established pattern of the user's normal routine.

For example, the user may be an Alzheimer's patient that has lucid moments and moments of memory loss. As has been established as a movement pattern by the wearable device, the patient takes a walk around the block every morning. However, if the patient wanders two blocks over and outside of the user's predetermined geo-fenced area, which is a deviation from the patient's normal pattern of movements, the system may alert the patient's caregiver of the inconsistency between the patient's current actions and the previously established patterns.

Monitor Compliance with Medicine Regime

The system, in a particular example, will also monitor the user's compliance with a medicine regime. In order to establish the user's medicine regime pattern, the user may wear the wearable device to detect when the user takes medicine and what medicine is taken using the front-facing camera. The user may also speak the name of the medicine as the wearable device captures an image of the medicine the user is taking The system is then able to establish a pattern of the user taking blood pressure medicine every morning after monitoring the user for a week. The system may then monitor the user's current medicine intake to compare the medicines the user takes and the time that the user takes the medicine to the previously established medicine regime pattern. If the user fails to take the blood pressure medicine on a particular morning, the system may notify the user, the user's caregiver, a health care provider, or a third party that the user has deviated from the previously established medicine regime.

CONCLUSION

Many modifications and other embodiments of the invention will come to mind to one skilled in the art to which this invention pertains, having the benefit of the teaching presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. A computer-implemented method of monitoring the wellbeing of an individual, the method comprising the steps of:
   a. providing a user with computerized eyewear comprising at least one sensor for monitoring the motion of the user;
   b. receiving, by one or more processors, a pre-defined command from the user, for the at least one sensor to generate a first set of data identifying one or more user-defined movement patterns for the user;
   c. in response to receiving the pre-defined command, collecting, by one or more processors, via the at least one sensor, the first set of data;
   d. using, by one or more processors, the first set of data to determine one or more typical movement patterns of the user;
   e. generating, by one or more processors, an established one or more user-defined movement patterns for the user based on the first set of data generated by the at least one sensor after the user with the computerized eyewear provides the pre-defined command for the at least one sensor to generate the first set of data identifying the one or more user-defined movement patterns for the user;
   f. receiving, by one or more processors, a second set of data generated by the at least one sensor after the established one or more user-defined movement patterns have been generated;
   g. at least partially in response to receiving the second set of data generated by the at least one sensor, determining, by one or more processors, the user's movements using the received second set of data;
   h. at least partially in response to determining the user's movements, comparing, by one or more processors, the user's movements based on the second set of data to the previously established one or more user-defined movement patterns for the user;
   i. detecting, by one or more processors, one or more inconsistencies between the current user's determined movements as compared to the previously established one or more user-defined movement patterns;
   j. at least partially in response to detecting the one more inconsistencies, notifying, by one or more processors, at least one recipient of the one or more inconsistencies, where the at least one recipient is a recipient selected from a group consisting of: the user and a third party.

2. The computer-implemented method of claim 1, wherein the at least one sensor comprises at least one sensor selected from a group consisting of:
   a. a motion sensor;
   b. an accelerometer;
   c. a gyroscope;
   d. a geomagnetic sensor;
   e. a global positioning system sensor;
   f. an impact sensor;
   g. a microphone;
   h. a forward facing camera;
   i. a heart rate monitor;
   j. a pulse oximeter;
   k. a blood alcohol monitor;
   l. a respiratory rate sensor; and
   m. a transdermal sensor.

3. The computer-implemented method of claim 2, wherein the at least one sensor comprises at least one sensor selected from a group consisting of: a motion sensor, an accelerometer, a global positioning sensor, a gyroscope, and a forward facing camera.

4. The computer-implemented method of claim 2, wherein the method further comprises the step of:
   a. calculating, by a processor, a number of steps taken by the user in a particular day;
   b. at least partially in response to calculating the number of steps, comparing, by a processor, the calculated number of steps taken by the user in the particular day to a predetermined average number of steps taken by the user in a day; and
   c. at least partially in response to comparing the calculated number of steps to the predetermined average number of steps, notifying the user or a third party if the calculated number of steps in the particular day is less than a predetermined percentage of the predetermined average number of steps taken by the user in a day.

5. The computer-implemented method of claim 2, further comprising the steps of:
   a. detecting, by a processor, whether the user moves during a predefined time period; and
   b. at least partially in response to detecting whether the user moves during the predefined time period, notifying, by a processor, the at least one recipient selected from a group consisting of: the user or a third party if the user does not move during the predefined time period.

6. The computer-implemented method of claim 2, further comprising the steps of:
   a. detecting, by a processor, from the received data generated by the at least one sensor if the user experiences a sudden acceleration or sudden impact; and
   b. at least partially in response to detecting that the user has experienced a sudden acceleration or sudden impact, notifying, by a processor, the user or a third party that the user experienced the sudden acceleration or sudden impact.

7. The computer-implemented method of claim 2, further comprising the steps of:
   a. detecting, by a processor, from the received data generated by the at least one sensor: (1) whether the user is breathing; and (2) whether the user's heart is beating; and
   b. at least partially in response to determining that the user is not breathing or that the user's heart is not beating, sending a notification to a third party.

8. The computer-implemented method of claim 2, further comprising the steps of:
   a. receiving, by a processor, from the user or third party, a medicine regime associated with the user;
   b. storing, by a processor, the medicine regime in memory;
   c. receiving, by a processor, data generated by a forward facing camera associated with the computerized eyewear;
   d. analyzing, by a processor, the received data to determine data selected from a group consisting of one or more:
      i. types of medicine taken by the user;
      ii. times the medicine is taken by the user; and
      iii. doses of the medicine taken by the user;
   e. at least partially in response to analyzing the received data, comparing, by a processor, the one or more of the types of medicine taken, the one or more times the medicine is taken, or the one or more doses of medicine taken to the stored medicine regime for the user;
   f. at least partially in response to comparing the one or more of the type of medicine taken, the time the medicine is taken and the dose of medicine taken, identifying, by a processor, one or more inconsistencies between the stored medicine regime, and the one or more types of medicine taken, the one or more times the medicine is taken, or the one or more doses of medicine taken;
   g. at least partially in response to identifying the one or more inconsistencies between the medicine regime and the one or more of the types of medicine taken, the one or more times the medicine is taken, or the one or more doses of medicine taken, sending an alert to the user or a third party of the one or more inconsistencies.

9. The computer-implemented method of claim 8, wherein:
   a. the data generated comprises one or more images captured by the forward facing camera;
   b. the step of analyzing the received data further comprises:
      i. detecting, by a processor, one or more pills in the one or more images;
      ii. comparing, by a processor, the one or more detected pills found in the one or more images to one or more known images of pills stored in a database;
      iii. identifying, by a processor, the one or more pills by matching the one or more pills from the one or more images to the one or more known images of pills stored in the database; and
      iv. detecting, by a processor, a time that the one or more images were taken.

10. A computer-implemented method of monitoring the wellbeing of an individual, the method comprising the steps of:
   a. providing a user with computerized eyewear comprising at least one sensor for monitoring actions taken by a user, the at least one sensor including a forward-facing camera that is a component of the computerized eyewear and is configured to automatically capture image data;
   b. receiving, by a processor, a medicine regime associated with the user;
   c. receiving, by a processor, data generated by the at least one sensor including image data automatically captured by the forward-facing camera of the computerized eyewear;
   d. analyzing, by a processor, the received data generated by the at least one sensor to determine data that identifies:
      i. types of medicine taken by the user based on image data automatically captured by the forward-facing camera that is a component of the computerized eyewear;
      ii. times the medicine is taken by the user; and
      iii. doses of medicine taken by the user based on image data automatically captured by the forward-facing camera that is a component of the computerized eyewear;
   e. at least partially in response to analyzing the received data generated by the at least one sensor, comparing, by a processor, the medicine regime for the user to the determined types of medicine taken by the user based on image data automatically captured by the forward-facing camera that is a component of the computerized eyewear, times the medicine is taken by the user, and doses of medicine taken by the user based on image data automatically captured by the forward-facing camera that is a component of the computerized eyewear;

f. detecting, by a processor, one or more inconsistencies between the medicine regime associated with the user and the determined types of medicine taken by the user based on image data automatically captured by the forward-facing camera that is a component of the computerized eyewear, times the medicine is taken by the user, and doses of medicine taken by the user based on image data automatically captured by the forward-facing camera that is a component of the computerized eyewear;

g. at least partially in response to detecting one or more inconsistencies between the medicine regime associated with the and the determined types of medicine taken by the user based on image data automatically captured by the forward-facing camera that is a component of the computerized eyewear, the medicine is taken by the user, and doses of medicine taken by the user based on image data automatically captured by the forward-facing camera that is a component of the computerized eyewear, notifying, by a processor, at least one recipient of the detected inconsistencies, where the at least one recipient is selected from a group consisting of: the user and the third party.

11. The computer-implemented method of claim 10, wherein the at least one sensor further comprises one or more sensors selected from a group consisting of: a scanner, a motion sensor, and a microphone.

12. The computer-implemented method of claim 10, wherein:
   a. the data generated is one or more images automatically captured by a forward facing camera;
   b. the step of analyzing the received data further comprises:
      i. detecting, by a processor, one or more pills in the one or more images;
      ii. comparing, by a processor, the one or more detected pills found in the one or more images to one or more known images of pills stored in a database;
      iii. identifying, by a processor, the one or more pills by matching the one or more pills from the one or more images to the one or more known images of pills stored in the database; and
      iv. detecting, by a processor, a time that the one or more images were taken.

13. The computer-implemented method of claim 10, further comprising the step of:
   a. detecting, by a processor, a level of one or more medicines in the user's bloodstream by at least one sensor of the computerized eyewear that monitors the level of one or more medicines in the user's bloodstream;
   b. comparing, by a processor, the level of the one or medicines in the user's bloodstream to a predefined level for each of the one or more medicines stored in a database for the user; and c. at least partially in response to comparing the level of the one or medicines in the user's bloodstream, notifying the at least one recipient when the level of the one or more medicines is below the predefined level for each of the one or more medicines, where the at least one recipient is selected from a group consisting of: the user and a third party.

14. The computer-implemented method of claim 10, further comprising the steps of:

a. determining, by a processor, the user's one or more movements using the received data generated by the at least one sensor;

b. analyzing, by a processor, the received data generated by the at least one sensor to determine the one or more movements associated with the user;

c. at least partially in response to analyzing the received data, comparing, by a processor, the user's one or more movements to previously established one or more movement patterns for the user;

d. detecting, by a processor, one or more inconsistencies between the user's one or more movements as compared to the previously established one or more movement patterns; and e. at least partially in response to detecting one or more inconsistencies between the current user's one or more movements as compared to previously established one or more movement patterns, notifying, by a processor, at least one recipient selected from a group consisting of: the user or a third party of the detected one or more inconsistencies.

15. A computer-implemented method of monitoring the wellbeing of an individual, the method comprising the steps of:
   a. providing a user with computerized eyewear comprising at least one sensor for monitoring actions taken by a user, the at least one sensor including:
      i) a sound-capturing unit that is a component of the computerized eyewear and that is configured to capture sound data,
      ii) a forward-facing camera that is a component of the computerized eyewear and that is configured to capture image data,
      iii) a location-determination unit that is a component of the computerized eyewear and that is configured to capture location data;
   b. receiving, by one or more processors, a medicine regime associated with the user, wherein the medicine regime is provided by:
      i) at least one of a group of users consisting of: (1) the user and (2) the user's physician, stating a name for each medicine in the medicine regime such that the sound-capturing unit of the computerized eyewear captures sound data for the name of each medicine in the medicine regime; and
      ii) the forward-facing camera of the computerized eyewear capturing image data of each medicine of the medicine regime and the medicine bottle for each medicine of the medicine regime;
   c. storing, by one or more processors, sound data and image data for the provided medicine regime in a database;
   d. receiving, by one or more processors, data generated by the at least one sensor including image data captured by the forward-facing camera of the computerized eyewear;
   e. analyzing, by one or more processors, the received data generated by the at least one sensor to determine at least image data that identifies:
      i) a first type of medicine taken by the user at a first geographic location, wherein the determination of the first type of medicine taken by the user is based on image data captured by the forward-facing camera and the determination of the first geographic location is based on location data captured by the location-determination unit;

ii) a first time that the first type of medicine was taken by the user at the first geographic location; and iii) a first dose of the first type of medicine taken by the user at the first geographic location based on image data captured by the forward-facing camera that is a component of the computerized eyewear;

f. analyzing, by one or more processors, the received data generated by the at least one sensor to determine at least image data that identifies:

i) a second type of medicine taken by the user at a second geographic location, wherein
the determination of the second type of medicine taken by the user is based on image data captured by the forward-facing camera and the determination of the second geographic location is based on location data captured by the location-determination unit, and
the first type of medicine is different from the second type of medicine, and the first geographic location is different from the second geographic location ii) a second time that the second type of medicine was taken by the user at the second geographic location; and iii) a second dose of the second type of medicine taken by the user at the second geographic location based on image data captured by the forward-facing camera that is a component of the computerized eyewear;

g. at least partially in response to analyzing the received data generated by the at least one sensor, comparing, by one or more processors, the medicine regime for the user to:

i) the determined first type of medicine taken by the user at the first geographic location, the first time that the first type of medicine was taken, and the first dose of the first type of medicine that was taken, and ii) the determined second type of medicine taken by the user at the second geographic location, the second time that the second type of medicine was taken, and the second dose of the second type of medicine that was taken;

h. detecting, by one or more processors, one or more inconsistencies between the medicine regime associated with the user and i) the determined first type of medicine taken by the user at the first geographic location, the first time that the first type of medicine was taken, and the first dose of the first type of medicine that was taken, or ii) the determined second type of medicine taken by the user at the second geographic location, the second time that the second type of medicine was taken, and the second dose of the second type of medicine that was taken;

i. at least partially in response to detecting the one more inconsistencies, notifying, by one or more processors, at least one recipient of the one or more inconsistencies, where the at least one recipient is a recipient selected from a group consisting of: the user and a third party.

16. The computer implemented method of claim 15, wherein the steps of determining the first type of medicine taken by the user at the first geographic location and determining the second type of medicine taken by the user at the second geographic location further comprise:

a. detecting, by one or more processors, one or more pills from the image data;

b. comparing, by one or more processors, the one or more detected pills found from the image data to one or more known images of pills stored in the database; and c. identifying, by one or more processors, the one or more pills by matching the one or more pills from the image data to the one or more known images of pills stored in the database.

17. The computer-implemented method of claim 15, further comprising the steps of:

a. detecting, by one or more processors, a level of one or more medicines in the user's bloodstream by at least one sensor of the computerized eyewear that monitors the level of one or more medicines in the user's bloodstream;

b. comparing, by one or more processors, the level of the one or medicines in the user's bloodstream to a predefined level for each of the one or more medicines stored in a database for the user; and c. at least partially in response to comparing the level of the one or medicines in the user's bloodstream, notifying the at least one recipient when the level of the one or more medicines is below the predefined level for each of the one or more medicines, where the at least one recipient is selected from a group consisting of: the user and a third party.

18. The computer-implemented method of claim 15, further comprising the steps of:

a. determining, by one or more processors, the user's one or more movements using the received data generated by the at least one sensor;

b. analyzing, by one or more processors, the received data generated by the at least one sensor to determine the one or more movements associated with the user;

c. at least partially in response to analyzing the received data, comparing, by one or more processors, the user's one or more movements to previously established one or more movement patterns for the user;

d. detecting, by one or more processors, one or more inconsistencies between the user's one or more movements as compared to the previously established one or more movement patterns; and e. at least partially in response to detecting one or more inconsistencies between the current user's one or more movements as compared to previously established one or more movement patterns, notifying, by one or more processors, at least one recipient selected from a group consisting of: the user or a third party of the detected one or more inconsistencies.

19. The computer-implemented method of claim 1, wherein the pre-defined command is defined by the user.

* * * * *